United States Patent [19]

Gion et al.

[11] Patent Number: 4,754,019

[45] Date of Patent: Jun. 28, 1988

[54] METHOD OF PRODUCING SUBSTANTIALLY PURE ALBUMIN USING CARBOXYLIC ACIDS AND AMMONIUM SULFATE

[75] Inventors: Yoshihiko Gion, Amagasaki; Yasuo Uehara, Otsu; Minoru Inosaka, Kyoto; Sadao Yabushita, Daito, all of Japan

[73] Assignee: The Green Cross Corporation, Osaka, Japan

[21] Appl. No.: 61,308

[22] Filed: Jun. 12, 1987

[30] Foreign Application Priority Data

Jun. 13, 1986 [JP] Japan .................................. 61-138492

[51] Int. Cl.$^4$ ..................... C07K 15/06; C07K 3/24; A61K 35/16
[52] U.S. Cl. ........................... 530/364; 424/101; 530/380; 530/386; 530/392; 530/394; 530/830; 530/831
[58] Field of Search ................ 424/101; 530/380, 386, 530/392, 394, 364, 830, 831

[56] References Cited

U.S. PATENT DOCUMENTS

| | | | |
|---|---|---|---|
| 2,705,230 | 3/1955 | Reid | 530/364 |
| 2,765,299 | 10/1956 | Porsche et al. | 530/364 |
| 3,100,737 | 8/1963 | Auerswald et al. | 530/364 Y |
| 3,926,939 | 12/1975 | Ivanov et al. | 530/364 |
| 3,992,367 | 11/1976 | Plan et al. | 530/364 |
| 4,017,470 | 4/1977 | Izaka et al. | 530/364 X |
| 4,025,500 | 5/1977 | Garcia et al. | 530/364 |
| 4,156,681 | 5/1979 | Schneider et al. | 530/364 |
| 4,169,829 | 10/1979 | Plan et al. | 530/364 |
| 4,177,188 | 12/1979 | Hansen | 530/364 |
| 4,613,501 | 9/1986 | Horowitz | 424/101 X |

Primary Examiner—Howard E. Schain
Attorney, Agent, or Firm—Cushman, Darby & Cushman

[57] ABSTRACT

High purity albumin can be recovered in high yield from human plasma protein solution containing albumin by heat-treatment of the solution to denature and precipitate non-albumin proteins in a combination of specific conditions such as protein concentration of the solution, pH, heating time and temperature, the concentration of precipitant ammonium sulfate.

12 Claims, No Drawings

METHOD OF PRODUCING SUBSTANTIALLY PURE ALBUMIN USING CARBOXYLIC ACIDS AND AMMONIUM SULFATE

This invention relates to a process for recovering albumin from a protein solution containing albumin of the human plasma origin which comprises subjecting the protein solution to a heat-treatment.

Albumin is a plasma protein which is contained in the plasma in a major amount, and is used against various disorders (such as scalding, nephrose, hemorrhagic shock, etc.).

Albumin is prepared in industry from the fine fraction V obtained by the Cohn's cold alcohol fractionation method. However, it is known that more or less amounts, that is 10 to 40 w/v %, of albumin is contained in a valuable plasma protein fraction or a fraction to be discarded which occurs from the valuable fraction after the valuable plasma proteins have been recovered.

A method of the purification of albumin in such fractions is disclosed in U.S. Pat. Nos. 4,017,470 to Izaka et al and 4,156,681 to Schneider et al. The both methods utilize the heat-stability of albumin as compared with other proteins and is carried out by heating an aqueous solution of the fraction at a temperature of 50° or higher to denature and precipitate proteins other than albumin. During the heating step a fatty acid or its salt is added as a stabilizer for albumin. The precipitation of the other proteins is accelerated by the addition of a specific amount of alcohol (U.S. Pat. No. 4,156,681). Albumin is recovered from the supernatant by a known method such as precipitation with polyethylene glycol, maleic acid or rivanol (2-ethoxy-6,9-diaminoacridine lactate) (U.S. Pat. No. 4,017,470).

In such methods, problems are present in the purity and recovering yield of albumin so that the product having a property sufficient for use as an albumin preparation in a good yield can not be obtained.

Thus, the present inventors have conducted an extensive study of the heat-treating methods or conditions in the recovery of pure albumin in good yield from an albumin containing plasma protein solution, especially $\alpha$- and/or $\beta$-globulin contaminated albumin solution of human plasma origin, and as a result, found that the above problem is solved by subjecting the solution to heat-treatment in a combination of specific conditions to recover effectively substantially pure albumin in high yield without above-mentioned drawbacks to achieve the present invention.

The present invention relates to a method for recovering a substantially pure albumin solution from a protein solution containing albumin and other plasma proteins of human origin, which comprises heating the protein solution at a temperature of 65° to 70° C. and pH of 4.5 to 5.5, preferably 4.9 to 5.4 for 15 to 60 minutes in the presence of 3 to 10 mM of an organic carboxylic acid having 3 to 10 carbon atoms or its salt and 1 to 10 w/v % of ammonium sulfate to precipitate proteins other than albumin, the protein solution being a solution containing the proteins in a concentration of 0.5 to 3 w/v %, and then recovering albumin from the supernatant.

(1) Starting material

The starting material used in the present invention is not limited to any of fractions as far as it contains albumin of human plasma origin but in general a fraction containing $\alpha$- and/or $\beta$-globulin is preferably mentioned. The fraction corresponds, for example, to the fraction IV, IV-1 or IV-4 of the Cohn's ethanol fractionation method, and to a precipitate fraction such as crude albumin responsive to 35 to 50% saturation of the ammonium sulfate.

(2) Pretreatment

The above-fractions can be used as they are in the present method, but a solution from which the other valuable proteins such as haptoglobin and others have been extracted and recovered is preferable. For example, haptoglobin is removed and recovered by precipitating out of the solution with ammonium sulfate saturation of 50% and then the supernatant is made into pH 4.5 to 4.8, the precipitates formed is recovered. The precipitates naturally contains ammonium sulfate which has been utilized.

3. Treatment

The albumin containing fraction mentioned in above (1) or (2) contains generally 10 to 70% of albumin and is dissolved in about 5—about 20 volume of an aqueous medium, preferably cold pure water so that the resulting solution contains 0.5-3% w/v proteins. To the solution is added an organic carboxylic acid or its salt as albumin stabilizer and ammonium sulfate as precipitating agent for proteins other than albumin.

The organic carboxylic acid is not limited as far as it has 3–10 carbon atoms, and a carboxylic acid such as caprylic acid, mandelic acid or citric acid is mentioned. The salt is physiologically acceptable one such as an alkali metal such as sodium or potassium, or an alkali earth metal such as calcium, etc. According to the invention, the organic carboxylic acid is used in a final concentration of 3–10 mM, preferably 3–5 mM.

Ammonium sulfate is used in a final concentration of 1–10% w/v, and when the albumin solution contains already ammonium sulfate, as the material mentioned in above (2), the amount should be taken into consideration.

The solution containing albumin is adjusted to pH 4.5–5.5, preferably 4.9–5.4 and further preferably 5.0–5.3, and then heated at a temperature of 65°–70° C., preferably about 68° C. for 15–60 minutes, preferably about 30 minutes.

After heating, the solution is cooled to about 10 to about 20° C., filtered or centrifuged at 5000–15,000 r.p.m. (4,500–13,000 G) for about 30 minutes to recover a supernatant. The filtration or centrifugation is preferably carried out at pH about 4–6. A precipitation fraction separated from the supernatant contains heat-coagulated proteins other than albumin.

(4) After-treatment

The supernatant contains very pure albumin having a purity of 90% or more, for example, up to 98% and can be used for making an albumin preparation as it is. However, it may be subjected to a known method for purifying and making preparation. For example, it is treated with an ion-exchanger, subjected to removing salt present for purification, and to heat-treatment at 60° C. for 10 hours for virus inactivation. Alternatively or if required, the methods disclosed in U.S. Pat. Nos. 4,156,681 and/or 4,017,470 can be used for the purification.

According to the present method, a high purity albumin can be obtained in high yield. Accordingly, an albumin preparation of high quality, which is applicable to clinical use, can be provided.

The present invention is explained concretely by way of the following examples which are not construed to limit the invention.

EXAMPLE 1

To 1 kg of fraction IV-4 paste containing 20% albumin and 80% other proteins was added 9 l of distilled water, stirred for 2 hours to obtain a solution which was then centrifugalized to separate a supernatant (pH 7.0). To the supernatant were added ammonium sulfate to a final concentration of 10% w/v, and sodium caprylate to a final concentration of 4 mM. The solution was adjusted in a pH of 5.2, then heated at 68° C. for 30 minutes, and cooled to 20° C. The pH was adjusted to 4-6, and then precipitates formed were removed by centrifuge. The separated supernatant contained 97% purity albumin in a recovery yield 90%.

EXAMPLE 2

Haptoglobin was precipitated from the Cohn's IV fraction solution (pH 7.0) by the ammonium sulfate fractionation method. The supernatant which was to be a waste and contained 30% w/v ammonium sulfate was adjusted to near the isoelectric point of albumin, pH 4.55, to precipitate albumin which was recovered as a crude albumin paste fraction.

To 1 kg of the paste fraction containing 60% albumin and 40% other proteins was added 9 l of distilled water to dissolve the fraction. Then the remaining ammonium sulfate contained in resulting solution was 2% w/v in a final concentration. To the solution was added sodium caprylate in a final concentration of 4 mM.

The solution was adjusted in pH 5, heated at 68° C. for 30 minutes, and then cooled to 20° C. to obtain precipitates which was then separated by centrifuge.

Albumin contained in the solution had a purity of 98% and was showed recovery yield 90%.

EXPERIMENTAL EXAMPLE 1

The relationship between protein concentration in the solution and albumin recovery was investigated.

Example 2 was repeated except for using a varying protein concentrations. The amount of albumin in total amounts of proteins was measured according to cellulose acetate membrane electrophoretic method (Kohn, J. Clin. Chim. Acta. 2 297 (1957)), and the total amount of proteins was measured according to ultra violet adsorption method (Tombs et al, Biochem. J. 73 167, (1959)).

TABLE 1

| Protein concentration in solution used (w/v %) | Albumin recovering yield (%) |
| --- | --- |
| 5 | 40 |
| 3 | 70 |
| 1 | 90 |
| 0.5 | 90 |

EXPERIMENTAL EXAMPLE 2

The relationship between the concentration of organic carboxylic acid and recovery of albumin.

Example 2 was repeated except for varying concentrations of the carboxylic acid used. The amount of albumin was measured by single radial immunodiffusion method (Mancini G, et al, Immunochemistry 2 235 (1965)).

The result is shown in Table 2.

TABLE 2

| Concentration of organic carboxylic acid (Sodium caprilate) (mM) | Recovering yield (%) |
| --- | --- |
| 0 | 10 |
| 1 | 64 |
| 2 | 73 |
| 4 | 90 |
| 8 | 90 |

EXPERIMENTAL EXAMPLE 3

The relationship between pH of the solution and the purity of albumin obtained was investigated.

Example 2 was repeated except for use of varying pH values. The amount of albumin recovered was measured by the single radial immunodiffusion method, and the purity of albumin was measured by the cellulose-acetate membrane electrophoresis method.

Result is shown in Table 3.

TABLE 3

| pH | Recovery yield (%) | Purity (%) | Evaluation |
| --- | --- | --- | --- |
| 4 | 0 | — | bad |
| 4.9 | 55 | 97 | pretty good |
| 5 | 80 | 96 | good |
| 5.1 | 95 | 92 | good |
| 5.3 | 100 | 90 | good |
| 6 | 100 | 80 | bad |

EXPERIMENTAL EXAMPLE 4

The influence of concentrations of ammonium sulfate was investigated.

Example 1 was repeated except for using a varying concentration of ammonium sulfate. The amount of the albumin recovery was measured based on the ultra-violet ray absorption method, and the purity of albumin was measured by the cellulose-acetate membrane electrophoresis method.

The result is shown in Table 4.

TABLE 4

| Concentration of sodium sulfate (w/v %) | Purity of albumin in supernatant (%) | Recovery yield (%) |
| --- | --- | --- |
| 0 | 80 | 85 |
| 1 | 90 | 90 |
| 5 | 95 | 92 |
| 10 | 97 | 90 |
| 15 | 85 | 80 |

EXPERIMENTAL EXAMPLE 5

The influence of heat-treatment times was investigated.

Example 2 was repeated except for using varying heating times. The amount of albumin recovered was measured by the single radial immunodiffusion method, and albumin purity was measured by the cellulose-acetate membrane electrophoresis method.

The result is shown in Table 5.

TABLE 5

| Heating time (min) | Purity of albumin obtained (%) | Recovery yield (%) |
| --- | --- | --- |
| 0 | 67 | 100 |
| 15 | 80 | 100 |
| 30 | 98 | 90 |
| 60 | 98 | 85 |

What is claimed is:

1. In a method of producing a substantially pure albumin solution from albumin and other plasma protein-containing solution comprising adding to the solution an organic carboxylic acid or physiologically acceptable salt thereof as an albumin stabilizer, a precipitating agent for the other plasma proteins, heating the solution at a temperature sufficient for denaturing and precipitating the other plasma protein and separating an albumin solution from the precipitates, the improvement comprising using the albumin and other plasma protein-containing solution having as protein concentration of 0.5 to 3% w/v, the organic carboxylic acid having 3 to 10 carbon atoms in an amount of 3–10 mM, and ammonium sulfate as the precipitating agent in a final concentration of 1 to 10% w/v; the heating being carried out for 15 to 60 minutes at a pH of 4.5 to 5.5 and at a temperature of 65° to 70° C.

2. The method according to claim 1, wherein the albumin and other plasma protein-containing solution contains $\alpha$- and/or $\beta$-globulin.

3. The method according to claim 1, wherein the albumin and other plasma protein-containing solution occurs from the Cohn's fraction IV, IV-1 or IV-4 or its equivalent.

4. The method according to claim 1, wherein the albumin and other plasma protein-containing solution is one from which a valuable plasma protein has been recovered.

5. The method according to claim 1, wherein the heating is carried out at a pH of 4.9 to 5.4.

6. The method according to claim 1, wherein the amount of the organic carboxylic acid used is 3 to 5 mM.

7. The method according to claim 1, wherein the heating is carried out at a pH of 5.0 to 5.3.

8. The method according to claim 1, wherein the heating is carried out at a temperature of about 68° C.

9. The method according to claim 1, wherein the heating is carried out for about 30 minutes.

10. The method according to claim 1, wherein the separation of albumin solution is carried out at a temperature of 10° to 20° C.

11. The method according to claim 1, wherein the separated albumin solution is further subjected to purification steps.

12. The method according to claim 1, wherein the separated albumin solution is subjected to virus-inactivating heat treatment.

* * * * *